United States Patent
Komatsu et al.

(10) Patent No.: US 7,605,303 B2
(45) Date of Patent: Oct. 20, 2009

(54) STRESS-RESPONSIVE ROOT-SPECIFIC GENES

(75) Inventors: Setsuko Komatsu, Ibaraki (JP);
Tomokazu Koshiba, Tokyo (JP);
Shinichiro Sawa, Tokyo (JP); Makoto Hashimoto, Tokyo (JP)

(73) Assignee: National Institute of Agrobiological Sciences, Tsukuba-Shi, Ibaraki (JP)

( * ) Notice: Subject to any disclaimer, the term of this patent is extended or adjusted under 35 U.S.C. 154(b) by 597 days.

(21) Appl. No.: 10/515,095

(22) PCT Filed: May 20, 2003

(86) PCT No.: PCT/JP03/06274

§ 371 (c)(1),
(2), (4) Date: Aug. 8, 2005

(87) PCT Pub. No.: WO03/097837

PCT Pub. Date: Nov. 27, 2003

(65) Prior Publication Data

US 2008/0155715 A1 Jun. 26, 2008

(30) Foreign Application Priority Data

May 20, 2002 (JP) .............................. 2002-144877

(51) Int. Cl.
*A01H 1/00* (2006.01)
*C07H 21/04* (2006.01)
*C07K 14/415* (2006.01)
*C12N 15/00* (2006.01)

(52) U.S. Cl. ........................... 800/295; 435/6; 435/468; 435/419; 435/320.1; 530/370; 536/23.1; 536/23.6; 800/278

(58) Field of Classification Search .................... 435/6, 435/69.1, 468, 419, 320.1; 530/370; 536/23.6; 800/289, 295

See application file for complete search history.

(56) References Cited

FOREIGN PATENT DOCUMENTS

| JP | 7-184659 | | 7/1995 |
|---|---|---|---|
| JP | 067184659 | * | 7/1995 |
| WO | WO 01/42475 A1 | | 6/2001 |

OTHER PUBLICATIONS

Accession No. AAR82701, Meiji Seika Kaisha Ltd., JP07184659, Jul. 25, 1995, Database A_Geneseq_200808, Result 7.*
Genbank Accession No. BI812364, Nov. 1, 2001.
Borkird, C., et al., "Gene Expression Associated with Water-stress Adaptation of Rice Cells and Identification of Two Genes as HSP 70 and Ubiquitin," *Physiologia Plantarum,* 82:449-457, 1991.
Borkird, C., et al., "Differential Expression of Water-stress Associated Genes in Tissues of Rice Plants," *J. Plant Physiol.* 138(5):591-595, 1991.
Hashimoto, M., et al., "Analysis of Stress Responsible Proteins in Rice Roots," *J. of Plant Research* 115(Supplement):194, No. 449. Dec. 2002.
Moons, A., et al., "Antagonistic effects of Abscisic Acid and Jasmonates on Salt Stress-Inducible Transcripts in Rice Roots," *Plant Cell* 9(12):2243-59, Dec. 1997.
Genbank Accession No. AAF85972, Jul. 16, 2000.
McGee, J.D. et al., "Characterization of a *PR-10* Pathogenesis-Related Gene Family Induced in Rice During Infection with Magnaporthe grisea," *MPMI,* 14(7):877-86, 2001.

* cited by examiner

*Primary Examiner*—Phuong T Bui
(74) *Attorney, Agent, or Firm*—Seed IP Law Group PLLC

(57) ABSTRACT

The present inventors succeeded in cloning a rice stress-responsive gene, RSI1. They discovered that stress-responsive plants can be generated by using the isolated gene, or genes functionally equivalent thereto. The present invention is useful in fields such as plant breeding.

7 Claims, 5 Drawing Sheets

CCACGCGTCCGAGCAACTAGTAGTCTAGCTAAGCTATGTCTAGTGGTGTGATCAGTAGTGGTGTCAGGTAGGAAGTTGCAGGTGGGGATATATC

ACCAATGGCTCCGGTCAGCATCTCCGACGAGCGCGCCCGTCTCGGTGTCGGCGAGCGGGTGTGGAAGGTCTTCTC

CGACGCGCCCGCCATGCCCAAGGTTTGTGCCGGCTTCATCGACGCCATTGAGGTCGAGGGGGATGGCCGGGCGGG

CACTGTCACCACCATGAAGCTCAACCCTGCTGTGGATGATGGGGGGGTCATTCAAAACACGTGTGGTGGCACGTGA

CAACGCAGCTCACATTATCAAGTCAGAGGTTCTGATGTGCCGGGCCCGGAAGTAAAGTGGGCAAGCTCAAGTCGCA

CGTGACAGAGACGAAGATCGAGGCCCGGCTCCTTGCTTGGCCAAGATAAACGTGGAGTATGAGCTCGA

GGACGGGCGGCTCACTGTCGCCCGGAGAAGGAGAAGCTCATCCCTCGACGGCTACTTCGGCATGCTCAAGATGATCGA

GGACTACCTCGTCGCTCACCCTACCGAGTATGCTTAAAAATTGTCATAAACCAAAATAATATACATCCATCTCCG

TATTGCTGCTTCCTGATAATTAAATGTGAGCCACGACAAATCCAATCTTTTGTGGTGTTTGATTTTGTGAGA

GTGATTTGTGTTTGAGGTTATGTAAGAAATAAATCATAATTGTGATCGTGTTCTAAAAAAAAAAAAAAAA

FIG. 2

MAPVSISDERAVSVSAERVWKVFSDAPAMPKVCAGFIDAIEVEGDGGAGTVTTMKLNPAVDDGGSFKTRV

VARDNAAHIIKSEVLDVPAGSKVGKLKSHVTETKIEAAGAGSCLAKINVEYELEDGGSLSPEKEKLILDG

YFGMLKMIEDYLVAHPTEYA

FIG. 3

```
Sequences producing significant alignments:                              Score    E
                                                                        (bits)  Value
gp:AF274850_1  pathogenesis-related protein PR-10a [Oryza sativa]        224    2e-58
pir:T02973     probenazole-induced protein - rice>gp:D38170_1 proben...  224    3e-58
gp:AF274851_1  pathogenesis-related protein PR-10b [Oryza sativa ...     210    4e-54
gp:AF211850_1  pathogenesis-related protein PsemI [Pseudotsuga me...      71    3e-12
gp:AF038949_1  intracellular pathogenesis-related protein PinmIII...      69    2e-11
gp:AF197343_1  putative intracellular pathogenesis-related protei...      67    6e-11
gp:AF197342_1  putative intracellular pathogenesis-related protei...      67    6e-11
gp:AOCPR3A_1   pathogenesis related protein [Asparagus officinalis]       59    2e-08
prf:2120434A   LEDI-1 protein - Lithospermum erythrorhizon...             59    2e-08
pir:S47249     gene 1-Sc3 protein - European white birch>prf:2122374...   58    4e-08
```

FIG. 4

STRESS-RESPONSIVE ROOT-SPECIFIC GENES

TECHNICAL FIELD

The present invention relates to novel stress-responsive proteins derived from plant roots, genes encoding said proteins, and modifications of plants using said genes. This invention is useful in fields such as plant breeding.

BACKGROUND ART

Plant salt tolerance and drought resistance are key factors in agriculture and environmental conservation. About one-third of the Earth is presently regarded as dry land. Desertification of farmland and green space is progressing, and the percentage of dry land is expected to increase in the future. Considering that the world's population in 2050 is estimated to be over 150% of the present population, and the increasingly serious food problem, the development of cultivation techniques and crop varieties that grow on unfavorable land, especially on dry land, are matters of urgency. Salinization is a serious problem in farming dry land. Since evapotranspiration is greater than rain fall in dry climates, continuing irrigation in poor drainage conditions promotes the rising of salt-containing groundwater levels and the deposition of salts at the soil surface. As a result, excessive amounts of salt accumulate in the soil. Cases where agriculture was abandoned due to salt accumulation, such as the decline of the Tigris-Euphrates Civilization, have been known since ancient times, and even today, salt accumulation is often problematic. Thus, enhancing salt and drought tolerance in crops is an important challenge in the advancement of agriculture in dry and salinity-affected land (Tadano, T. (1983) Salt tolerance in crops and its mechanisms. Kagaku to Seibutsu 21, 439-445; Uchiyama, Y. (1988) Agricultural utilization of high-salt environments. Kagaku to Seibutsu 26, 650-659.).

If a gene responsive to a stress such as salt or drought can be isolated, the introduction of this gene to a given crop cultivar, by transformation methods or such, may enhance the cultivar's tolerance to salt and drought stresses in such systems.

The plant parts that are above ground, such as leaves and shoot apices, clearly play important roles in the environmental responses of plants. Roots too play a crucial part in stress tolerance, since, in conjunction with water and nutrient absorption, roots have regulatory mechanisms that respond to stresses such as drought, salt and low temperature.

Therefore, the isolation of genes in plant roots that respond to salt or drought stress was desired.

DISCLOSURE OF THE INVENTION

The present invention was achieved in view of this situation. An objective of this invention is to provide novel stress-responsive genes in plant roots. The genes of this invention are genes from monocotyledons, preferably from rice. Another objective of the present invention is to improve plants using these genes.

The present inventors carried out intensive research to achieve these tasks and to isolate and identify stress-responsive proteins in rice roots.

In this invention, as one part of the comprehensive research, the environment-responsive proteins in rice roots were analyzed using rice proteome analysis with a focus on drought, salt and abscisic acid.

Abscisic acid (ABA), a plant hormone, is known to be involved in important plant physiological functions, such as acquisition of stress response and tolerance to drought and low temperature, as well as seed maturation, dormancy, germination and such. Plants subjected to environmental stresses such as drought and low temperature are thought to acquire the ability to adapt to environmental stresses due to the in vivo synthesis of ABA, which causes various changes within the plant cells.

Specifically, the present inventors treated rice plants in their 14th day after seeding with abscisic acid and two kinds of stress, salt and drought, and discovered that stress-responsive proteins were present in proteins extracted from the roots. Of the candidate proteins, protein RO-292, the amount of which markedly increased on salt or drought treatment, was identified. The sequence of 16 amino acid residues from the N terminal of RO-292 was determined. The EST comprising the nucleotide sequence corresponding to this sequence was supplied from a DNA bank. The sequencing results of the full-length EST showed that it was a complete full-length cDNA. The amino acid sequence estimated from the full-length cDNA was about 68% homologous to the PR-10-like proteins and rice probenazole-induced protein.

Northern blot analysis after drought treatment confirmed a more remarkable induction of RO-292 gene expression in roots than in leaves. The present inventors named the RO-292 gene "Root Specific Induced gene" (RSI1).

While RSI1 responds to drought and salt stresses, it does not respond to abscisic acid. Therefore, this gene is useful to create environmental stress-resistant plants that are independent of abscisic acid.

Thus, the present inventors succeeded in isolating a stress-responsive gene RSI1, which is specifically expressed in plant roots and responds to salt or drought stress. Thus, the present invention was completed.

This invention relates to novel stress-responsive genes in plant roots, and more specifically, provides the following:

[1] a DNA that is plant-derived and described by any one of the following (a) to (d):
  (a) A DNA that encodes a protein comprising the amino acid sequence of SEQ ID NO: 2,
  (b) A DNA that comprises the coding region of the nucleotide sequence of SEQ ID NO: 1,
  (c) A DNA that encodes a protein comprising the amino acid sequence of SEQ ID NO: 2, in which one or more amino acid residues are substituted, deleted, inserted, and/or added,
  (d) A DNA that, under stringent conditions, hybridizes to a DNA comprising the nucleotide sequence of SEQ ID NO: 1;

[2] the DNA of [1], expression of which is induced by sodium chloride treatment;

[3] the DNA of [1], expression of which is induced by drought treatment;

[4] the DNA of [2] or [3], expression of which is not induced by abscisic acid treatment;

[5] a vector that comprises the DNA of [1];

[6] a transformed plant cell that retains the DNA of [1] in the expressible manner;

[7] a transgenic plant that comprises the transformed plant cell of [6];

[8] a transgenic plant that is a progeny or clone of the transgenic plant of [7];

[9] a propagation material of the transgenic plant of [7] or [8];

[10] a method for preparing the transgenic plants of [7] or [8], wherein the method comprises the steps of introducing the DNA of [1] into plant cells, and re-generating plants from said plant cells;

[11] a protein encoded by the DNA of any one of [1] to [4];

[12] an antibody that binds to the protein of [11]; and

[13] a polynucleotide that comprises at least 15 nucleotide residues, which is complementary to the DNA comprising the nucleotide sequence of SEQ ID NO: 1 or to the complementary strand thereof.

The present invention provides DNAs encoding the protein OsRSI1. The DNAs of this invention comprise the property to be expressed in response to plant stress. More specifically, they comprise the property of induced expression due to sodium chloride or drought treatment, but not abscisic acid treatment.

The plant species from which the DNAs of this invention are derived are not specifically limited, however, are usually monocotyledons, preferably rice.

The nucleotide sequence of the rice "RSI1" gene (OsRSI1) of the present invention is shown in SEQ ID NO: 1. Furthermore, the amino acid sequence of the protein encoded by the rice "RSI1" gene is shown in SEQ ID NO: 2.

The estimated amino acid sequence of the rice "RSI1" comprised significant homology (68.75%) to PR-10-like proteins and the rice probenazole-induced protein, which are known as proteins whose expression can be induced by stress (FIG. 4). Therefore, it is postulated that the "RSI1" protein plays important roles in plant stress responses. The DNAs of this invention are highly expected to be useful in creating salt-resistant or drought-resistant plant cultivars.

The DNAs of this invention include not only DNA species that encode naturally occurring "RSI1" proteins, but also DNA species that encode mutant proteins which are functionally equivalent to the RSI1 protein, and comprise the "RSI1" protein amino acid sequence (SEQ ID NO: 2), in which one or more amino acid residues is substituted, deleted, inserted, and/or added.

The DNAs encoding the RSI1 protein of this invention include genomic DNAs, cDNAs, and chemically synthesized DNAs. The preparation of the genomic DNAs and cDNAs can be conducted by using methods common to one skilled in the art. A genomic DNA can be prepared, for example, by extracting genomic DNAs from a rice cultivar comprising the RSI1 gene, constructing and developing a genomic library (plasmids, phages, cosmids, BAC, PAC and such can be used as vectors), and then obtaining the genomic DNA by colony or plaque hybridization using a probe prepared based on a DNA (for example, SEQ ID NO: 1) that encodes the protein of this invention. Alternatively, the genomic DNA can also be prepared by constructing a primer specific to a DNA (for example, SEQ ID NO: 1) that encodes the protein of this invention, and carrying out PCR using this primer. In addition, a cDNA can be prepared, for example, by synthesizing cDNAs from mRNA extracts of a rice cultivar that comprises the RSI1 gene, constructing and expanding a cDNA library by inserting the cDNAs into vectors such as λZAP, and then using colony or plaque hybridization as above, or PCR procedures, to obtain the cDNA.

The present invention comprises DNAs that encode proteins functionally equivalent to the RSI1 protein of SEQ ID NO: 2. The plant species from which the DNAs of this invention are derived are not specifically limited, but are preferably species belonging to Graminae, and most preferably rice. Herein, "functionally equivalent to RSI1 protein" means that the protein of interest comprises the function of being expressed in response to plant stress. More specifically, examples of functions can be given, where expression can be induced by sodium chloride or drought treatment. In these cases, it is preferable that abscisic acid treatment does not induce expression.

The DNAs of this invention comprise, for example, derivatives, alleles, variants, and homologs, and mutants that encode proteins comprising the amino acid sequence of SEQ ID NO: 2, in which one or more amino acid residues is substituted, deleted, added, and/or inserted.

Mutations can also be artificially introduced. Protein amino acid sequence mutations caused by mutations in the nucleotide sequence encoding the protein can take place naturally. Site-directed mutagenesis is an example, widely known to those skilled in the art, of a method for preparing DNAs that encode proteins with modified amino acid sequences (Kramer, W. & Fritz, H.-J. (1987) Oligonucleotide-directed construction of mutagenesis via gapped duplex DNA. Methods in Enzymology, 154: 350-367). Thus, DNAs encoding the amino acid sequence of naturally occurring type RSI1 protein, in which one or more amino acid residues are substituted, deleted, or added, are also included in the DNAs of this invention, so long as said DNAs encode proteins that comprise a function equivalent to that of naturally occurring RSI1 protein (SEQ ID NO: 2). Moreover, even when there is a mutation in the nucleotide sequence, it is possible that there is no change in the amino acid residues (degenerate mutations) Such degenerate mutants are also included in the DNAs of the present invention.

Whether or not a given DNA encodes a protein that comprises the function of being expressed in response to plant stress can be determined, for example, by analyzing whether or not the protein, or an mRNA encoding the protein, is induced in a stress-dependent manner in plants introduced with the DNA of interest. Specifically, this analysis can be carried out by analyzing the presence or absence of induced expression due to sodium chloride treatment or drought treatment.

Other methods, well known to those skilled in the art, for the preparation of DNAs that encode proteins functionally equivalent to the RSI1 protein of SEQ ID NO: 2, include methods using hybridization techniques (Southern, E. M. (1975) Journal of Molecular Biology, 98, 503) and polymerase chain reaction (PCR) techniques (Saiki, R. K. et al. (1985) Science, 230, 1350-1354; Saiki, R. K. et al. (1988) Science, 239, 487-491). In other words, those skilled in the art can isolate DNAs that are highly homologous to the RSI1 gene of rice or other plants, by using the RSI1 gene nucleotide sequence (SEQ ID NO: 1) or part thereof as a probe, or using oligonucleotides that specifically hybridize to the RSI1 gene as a primer. Thus, DNAs that can be isolated by hybridization techniques or PCR techniques, and that encode proteins comprising functions equivalent to the RSI1 protein, are also included in the DNAs of the present invention.

To isolate such DNAS, hybridization reactions are preferably performed under stringent conditions. In the present invention, stringent hybridization conditions are 6 M urea, 0.4% SDS, 0.5×SSC, or conditions equivalent to these. However, these conditions are not particularly limiting. DNA with higher homology can be expected to be isolated using conditions of higher stringency, for example 6 M urea, 0.4% SDS and 0.1×SSC. A number of factors, including temperature and salt concentration, are considered to affect hybridization stringency, and those skilled in the art can achieve optimal stringency by appropriately selecting these factors. DNAs thus isolated are considered to comprise high homology at the amino acid level to the amino acid sequence of the RSI1 protein (SEQ ID NO: 2). Here, high homology means that at least 50% of the entire sequence is identical, preferably 70% or above, and more preferably 90% or above (for example, 95% or above).

The sequence identity of amino acids or nucleotides can be determined by using BLAST, an algorithm developed by Karlin and Altschul (Karlin, S. & Altschul, S. F. (1990) Proc. Natl. Acad. Sci. USA, 87: 2264-2268; Karlin, S. & Altschul, S. F. (1993) Proc. Natl. Acad. Sci. USA, 90: 5873-5877). Programs called BLASTN and BLASTX have been developed based on the algorithm of BLAST (Altschul, S. F. et al. (1990) J. Mol. Biol., 215: 403). In the analysis of nucleotide sequences using BLASTN, the parameters are set at, for example, score=100 and wordlength=12. In the analysis of amino acid sequences using BLASTX, the parameters are set at, for example, score=50 and wordlength=3. When using the BLAST and Gapped BLAST programs, the default parameters for each program are used. The specific techniques of these analytical methods are widely known (ncbi.nlm.nih.gov).

Proteins encoded by the above-mentioned DNAs of this invention are also included in the present invention.

The DNAs of this invention can be used to produce transgenic plants with improved stress response and such, for example, improved response to salt stress or drought stress.

In general, when preparing recombinant proteins, a DNA encoding a protein of the present invention is inserted into an appropriate expression vector, this vector is introduced into appropriate cells, these transformed cells are cultured, and the expressed protein of interest is purified. For easier purification and such, the recombinant proteins can be expressed as fusion proteins with other proteins. For example, methods that can be applied when *E. coli* is the host (Vector pMAL Series, supplied by New England BioLab, U.S.A.) include preparation as a fusion protein with maltose-binding protein, preparation as a fusion protein with glutathione S-transferase (GST) (Vector pGEX Series, supplied by Amersham Pharmacia Biotech), and preparation with an attached histidine tag (pET Series, supplied by Novagen). The host cells are not particularly limited as long as they are suitable for the expression of recombinant proteins. Host cells such as yeasts, various animal cells, plant cells, and insect cells can be used as well as the above-described *E. coli*. The introduction of vectors into host cells can be carried out by various methods widely known to those skilled in the art. For example, vectors can be introduced into *E. coli* using an introduction method that uses calcium ions (Mandel, M. & Higa, A. (1970) Journal of Molecular Biology, 53, 158-162; Hanahan, D. (1983) Journal of Molecular Biology, 166, 557-580). Recombinant proteins expressed in host cells can be purified and collected from said host cells, or from the supernatant of the culture medium, using methods well known to those skilled in the art. When recombinant proteins are expressed as fusion proteins, such as with the above-described maltose-binding protein, affinity purification can be easily carried out.

The obtained recombinant proteins can be used to prepare antibodies against themselves. For example, polyclonal antibodies can be prepared by immunizing immune animals such as rabbits with a purified protein of this invention, or its partial peptide, collecting blood after a certain period, and then removing blood clots. Monoclonal antibodies can be prepared by fusing myeloma cells to antibody-producing cells from the animals immunized with the proteins or peptides, isolating target antibody-producing cells that are derived from a single clone (hybridomas), and generating antibodies from such cells. Antibodies obtained in this way can be used for the purification or detection of the proteins of the present invention. Antibodies against the proteins of the present invention are included in this invention.

When using the DNAs of the present invention to create transgenic plants with a modified stress response, for example, response to salt or drought stress, DNAs encoding proteins of this invention are inserted into appropriate vectors, these vectors are introduced into plant cells, and the transformed plant cells thus obtained are regenerated.

Vectors that can be used for the transformation of plant cells are not particularly limited, as long as expression of the introduced gene is possible in the cells. For example, usable vectors are vectors comprising promoters that allow a constitutive gene expression in plant cells (such as the cauliflower mosaic virus 35S promoter); or vectors comprising promoters whose activation is induced by external stimuli (such as infection or invasion by filamentous fungi, bacteria, or viruses, low temperature, high temperature, saline environments, drought, ultraviolet irradiation and spraying of certain chemicals). Examples of such promoters include the rice chitinase gene promoter or tobacco PR protein gene promoter (Ohshima et al. (1990) Plant Cell, 2, 95), which are expressed on infection or invasion by filamentous fungi, bacteria, or viruses (Xu et al. (1996) Plant Mol. Biol., 30, 387), the rice "lip19" gene promoter, which is induced by low temperature (Aguan et al. (1993) Mol. Gen. Genet., 240, 1), the rice "hsp80" gene and "hsp72" gene promoters, which are induced by high temperature (Van Breusegem et al. (1994) Planta, 193, 57), the Arabidopsis "rab16" gene promoter, which is induced by drought (Nundy et al. (1990) Proc. Natl. Acad. Sci. USA, 87, 1406), the parsley chalcone synthase gene promoter, which is induced by ultraviolet irradiation (Schlze-Lefert et al. (1989) EMBO J., 8, 651), and the corn alcohol dehydrogenase gene promoter, which is induced under anaerobic conditions (Walker et al. (1987) Proc. Natl. Acad. Sci. USA, 84, 6624). Furthermore, the rice chitinase gene promoter and tobacco PR protein gene promoter are also induced by certain chemical compounds, such as salicylic acid; and the "rab16" gene is induced by spraying abscisic acid, a plant hormone.

Here, "plant cells" includes various states and forms of plant cells; for example, cell culture suspensions, protoplasts, leaf cuttings, and calluses.

The introduction of vectors into plant cells can be carried out using various methods widely known to those skilled in the art, such as polyethylene glycol methods, electroporation methods, methods that utilize *Agrobacterium,* and particle gun methods. Plants can be regenerated from transformed plant cells using methods widely known to those skilled in the art, depending on the species and type of plant cell (Toki et al. (1992) Plant Physiol., 100, 1503-1507). For example, transgenic rice plants can be created by a number of established technologies, such as regenerating plants (indica cultivars are suitable) after introducing genes into protoplasts using polyethylene glycol (Datta, S. K. (1995) in Gene Transfer To Plants (Potrykus, I. and Spangenberg, G., eds.) pp. 66-74), regenerating plants after introducing genes into protoplasts using electric pulses (Toki et al. (1992) Plant Physiol., 100, 1503-1507), regenerating plants after directly introducing genes into cells using the particle gun method (Christou et al. (1991) Bio/technology, 9, 957-962), and regenerating plants after introducing genes using *Agrobacterium* (Ultra-rapid Method of Transformation of Monocotyledons (Japanese Patent no. 3141084)). These techniques are widely used in the art of the present invention, and can be applied suitably to this invention.

Having established a transgenic plant with a DNA of the present invention incorporated into its genome, offspring can be obtained from this plant by sexual or asexual reproduction. In addition, such plants can be mass-produced using propagation materials (for example, seeds, fruits, cuttings, tubers, tuberous roots, plant stubs, calluses, protoplasts etc.) derived from said plants, their offspring, or clones. The present invention includes plant cells in which the DNA of this invention is introduced, plants that comprise these cells, the offspring and clones of these plants, and the propagation material of these plants, their offspring, and clones. Compared to wild type plants, plants created in this way are considered to have an improved stress response, such as the stress response to salt and drought. The techniques of the present invention are very useful for improving the productivity of valuable agricultural crops such as rice.

The present invention also provides polynucleotides complementary to the DNAs of this invention, which comprise the nucleotide sequence of SEQ ID NO: 1, or to complementary strands thereof, where the polynucleotides comprise at least 15 nucleotide residues. Herein, "complementary strand" means the other chain corresponding to one of the two chains of a double-stranded DNA that consists of A:T and G:C base pairs. In addition, "complementary" is not limited to cases of complete complementarity to a continuous nucleotide region of at least 15 bases, but can also comprise nucleotide sequence homology of at least 70%, preferably at least 80%, more preferably at least 90%, and most preferably 95% or above. Such DNAs are useful as probes for detecting and isolating, and as primers for amplifying, the DNAs of this invention.

BRIEF DESCRIPTION OF THE DRAWINGS

FIG. 2 shows the nucleotide sequence of the full-length RO-292 cDNA (SEQ ID NO: 1). RO-292 is a gene that comprises 744 bases.

FIG. 3 shows the deduced amino acid sequence of RO-292 (SEQ ID NO: 2). RO-292 comprises 160 amino acid residues. The underlined region indicates the sequence APVSISDER-AVSVSAEXXXK (SEQ ID NO: 3) determined by peptide sequence analysis.

FIG. 4 shows the results of a BLAST search for proteins showing homology to the RO-292 amino acid sequence.

BEST MODE FOR CARRYING OUT THE INVENTION

Herein below, the present invention will be specifically described using Examples, however, it is not to be construed as being limited thereto.

Rice seedlings (Cultivar: Nipponbare) in their fourteenth day after seeding were treated with two types of stress, salt (100 mM NaCl, 24 hour treatment) and drought (drought treatment, 15 hours), and abscisic acid (0.1 mM ABA, 12 hours) whose biosynthesis is considered to be stress-induced. Proteins were then extracted from the roots. The patterns of two-dimensional electrophoresis of the extracted proteins were compared, and stress-responsive proteins were screened and detected. (Table 1).

TABLE 1

| Stress | Spots that showed an increase | Spots that showed a decrease |
|---|---|---|
| Salt treatment | RO-287, RO-288, RO-292 | RO-15 |
| Drought treatment | RO-287, RO-288, RO-292 | RO-198, RO-C |
| ABA treatment | RO-246, RO-278, RO-297, RO-A, RO-B, RO-281 | RO-38 |

In Table 1, RO-287, RO-288, and RO-292 are candidates for stress-responsive proteins that increase on salt and drought treatments. RO-281 is a new candidate protein selected by analyzing the two-dimensional electrophoresis patterns. RO-A, RO-B, and RO-C are spots not yet numbered.

Figure 1:
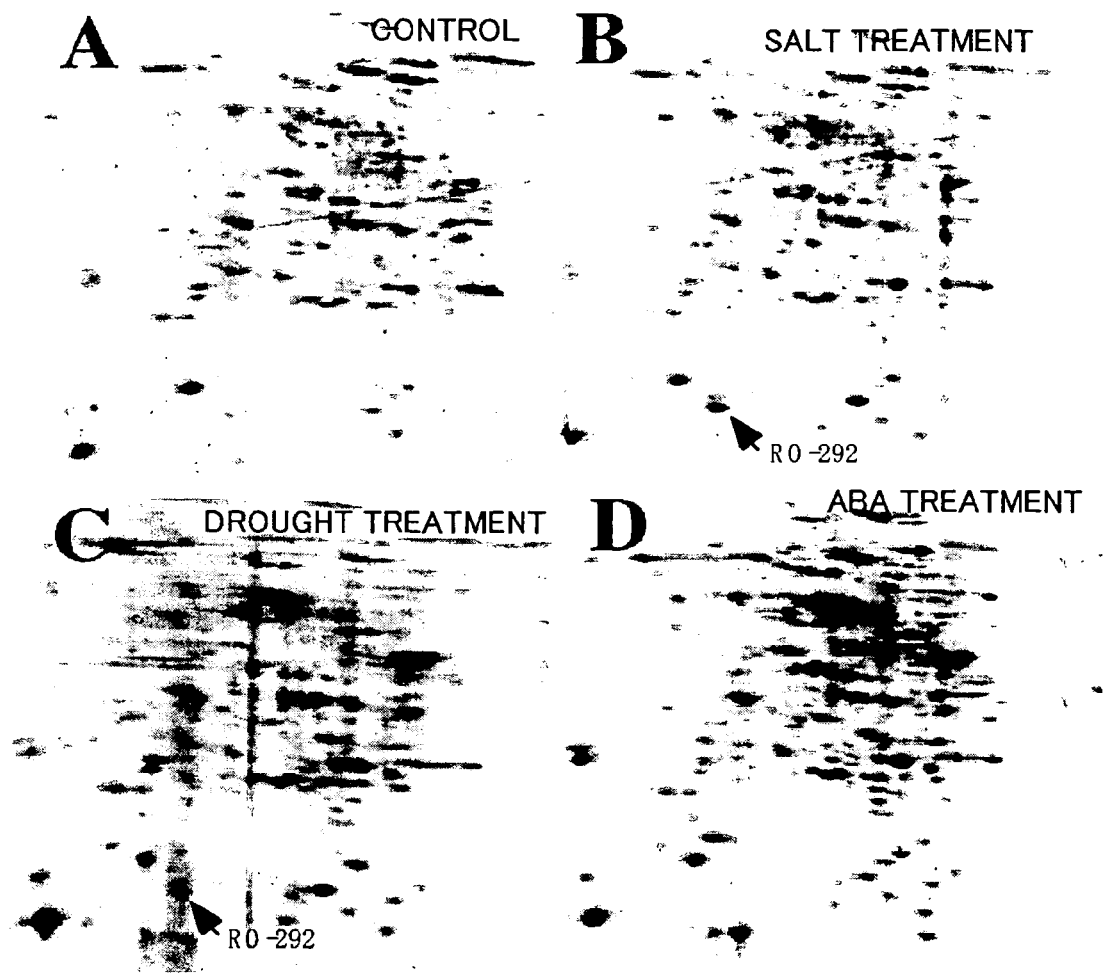
FIG. 1 shows photographs demonstrating the patterns of two-dimensional electrophoresis of rice-root proteins. A: control. B: salt treatment (100 mM NaCl, 24 hour treatment). C: drought treatment (drought treatment for 15 hours). D: ABA treatment (0.1 mM ABA, 12 hour treatment). RO-292 (which represents OsRSI1) showed significant induction on salt treatment and drought treatment.

As a result, RO-292 was identified as a protein markedly increased by drought and salt treatments (FIG. 1).

The 16 amino acid residue sequence from the N-terminal of RO-292 was determined. An EST comprising a nucleotide sequence identical to the above-mentioned amino acid sequence was obtained from a DNA bank, and the full-length EST was sequenced. The results indicated that this EST was a full-length cDNA (FIG. 2) and that it comprised the amino acid sequence determined by peptide sequencing (FIG. 3). The deduced amino acid sequence was 68.75% homologous to PR-10-like proteins and the rice probenazole-induced protein (FIG. 4).

Figure 5:
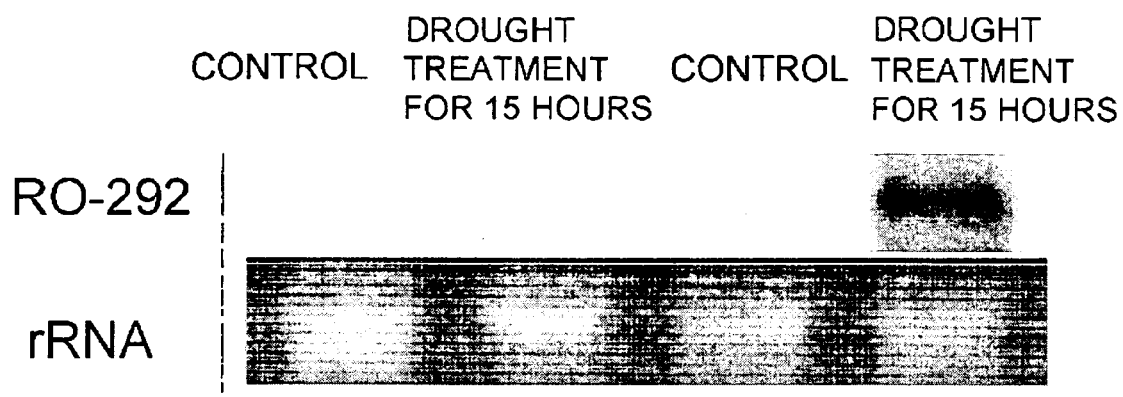
FIG. 5 shows photographs representing the results of Northern blot analysis of mRNA extracted from leaves and roots after 15 hours of drought treatment, to determine the drought response of the RO-292 gene. Induced expression was more remarkable in the roots than in the above-ground parts.

Furthermore, to analyze the level of RO-292 gene expression, drought treatment was performed under the same conditions as for proteome analysis, followed by Northern blot analysis. These results confirmed that induced expression was more remarkable in the roots than in the above-ground parts (FIG. 5).

The present inventors named the RO-292 gene "RSI1", as a root specific induced gene.

INDUSTRIAL APPLICABILITY

The isolated root-specific RSI1 gene of this invention is considered capable of rendering plants stress responsive through its expression in those plants.

As the genes of this invention respond to drought stress and salt stress, but do not respond to abscisic acid, they are useful in producing rice with abscisic acid-independent tolerance to environmental stresses. Therefore, for example, by introduction into valuable agricultural crops such as rice, the genes are expected to contribute to modifying stress responsiveness, avoiding salt damage even in dry land, and increasing the productivity of agricultural crops.

The invention claimed is:

1. An isolated DNA selected from the group consisting of:
   (a) an isolated DNA that encodes a protein comprising the amino acid sequence of SEQ ID NO:2;
   (b) an isolated DNA that comprises the coding region of the nucleotide sequence of SEQ ID NO:1;
   (c) an isolated DNA that encodes a protein comprising an amino acid sequence that has at least 95% identity to the amino acid sequence of SEQ ID NO:2, wherein said isolated DNA encodes a protein that is induced to be produced in a rice root in response to sodium chloride or drought but not abscisic acid; and
   (d) an isolated DNA that hybridizes to a complementary DNA comprising the nucleotide sequence complementary to that of SEQ ID NO:1 under stringent conditions of 6M urea, 0.4% SDS, and 0.1X SSC, wherein said isolated DNA encodes a protein that is induced to be produced in a rice root in response to sodium chloride or drought but not abscisic acid.

2. A vector that comprises the DNA of claim 1.

3. A transformed plant cell that retains the DNA of claim 1 in the expressible manner.

4. A transgenic plant that comprises the transformed plant cell of claim 3.

5. A transgenic plant that is a progeny or clone of the transgenic plant of claim 4.

6. A propagation material of a transgenic plant comprising a plant cell transformed with the isolated DNA of claim 1, wherein the propagation material retains the isolated DNA in an expressible manner.

7. A method for preparing a transgenic plant, wherein the method comprises the steps of introducing the solated DNA of claim 1 into a plant cell, and re-generating the transgenic plant from the plant cell.

* * * * *

UNITED STATES PATENT AND TRADEMARK OFFICE
CERTIFICATE OF CORRECTION

PATENT NO.       : 7,605,303 B2
APPLICATION NO. : 10/515095
DATED            : October 20, 2009
INVENTOR(S)      : Komatsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1077 days.

Signed and Sealed this

Fifth Day of October, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 744
<212> TYPE: DNA
<213> ORGANISM: Oryza sativa

<400> SEQUENCE: 1

```
ccacgcgtcc gagcaactag gtatctagct aagcagtggt gtgatcagta ggaagttgca      60
ggtgggggat atatcaccaa tggctccggt cagcatctcc gacgagcgcg ccgtctcggt     120
gtcggcggag cgggtgtgga aggtcttctc cgacgcgccc gccatgccca aggtttgtgc     180
cggcttcatc gacgccattg aggtcgaggg ggatggcggg cgggcactg tcaccaccat      240
gaagctcaac cctgctgtgg atgatggggg gtcattcaaa acacgtgtgg tggcacgtga     300
caacgcagct cacattatca agtcagaggt tctggatgtg ccggccggaa gtaaagtggg     360
caagctcaag tcgcacgtga cagagacgaa gatcgaggcc gccggtgccg gctcttgctt     420
ggccaagata aacgtggagt atgagctcga ggacggcggc tcactgtcgc cggagaagga     480
gaagctcatc ctcgacggct acttcggcat gctcaagatg atcgaggact acctcgtcgc     540
tcaccctacc gagtatgctt aaaaattgtc ataaaccaaa ataatataca tccatctccg     600
tattgctgct tcctgataat taaataatgt gagccacgac aaatccaatc ttttgtggtg     660
tttgattttg tgagagtgat ttgtgtttga ggttatgtaa gaaataaatc ataattgtga     720
tcgtgttcta aaaaaaaaaa aaaa                                            744
```

<210> SEQ ID NO 2
<211> LENGTH: 160
<212> TYPE: PRT
<213> ORGANISM: Oryza sativa

<400> SEQUENCE: 2

```
Met Ala Pro Val Ser Ile Ser Asp Glu Arg Ala Val Ser Val Ser Ala
1               5                   10                  15

Glu Arg Val Trp Lys Val Phe Ser Asp Ala Pro Ala Met Pro Lys Val
            20                  25                  30

Cys Ala Gly Phe Ile Asp Ala Ile Glu Val Glu Gly Asp Gly Gly Ala
        35                  40                  45

Gly Thr Val Thr Thr Met Lys Leu Asn Pro Ala Val Asp Asp Gly Gly
    50                  55                  60

Ser Phe Lys Thr Arg Val Val Ala Arg Asp Asn Ala Ala His Ile Ile
65                  70                  75                  80

Lys Ser Glu Val Leu Asp Val Pro Ala Gly Ser Lys Val Gly Lys Leu
                85                  90                  95

Lys Ser His Val Thr Glu Thr Lys Ile Glu Ala Ala Gly Ala Gly Ser
            100                 105                 110

Cys Leu Ala Lys Ile Asn Val Glu Tyr Glu Leu Glu Asp Gly Gly Ser
        115                 120                 125

Leu Ser Pro Glu Lys Glu Lys Leu Ile Leu Asp Gly Tyr Phe Gly Met
    130                 135                 140

Leu Lys Met Ile Glu Asp Tyr Leu Val Ala His Pro Thr Glu Tyr Ala
145                 150                 155                 160
```

<210> SEQ ID NO 3
<211> LENGTH: 20

-continued

```
<212> TYPE: PRT
<213> ORGANISM: Oryza sativa
<220> FEATURE:
<223> OTHER INFORMATION: Portion of RO-292 sequence determined by
      sequence analysis
<220> FEATURE:
<221> NAME/KEY: MOD_RES
<222> LOCATION: 17,18,19
<223> OTHER INFORMATION: Xaa indicates any or unknown amino acid

<400> SEQUENCE: 3

Ala Pro Val Ser Ile Ser Asp Glu Arg Ala Val Ser Val Ser Ala Glu
1               5                   10                  15

Xaa Xaa Xaa Lys
            20
```